US012667331B2

(12) United States Patent
Baumann et al.

(10) Patent No.: US 12,667,331 B2
(45) Date of Patent: Jun. 30, 2026

(54) METHOD AND DEVICE FOR DETERMINING INTRACRANIAL PRESSURE OF A PATIENT

(71) Applicant: COMPREMIUM AG, Bern (CH)

(72) Inventors: Ulrich Baumann, Münsingen (CH); Vincent Boris Baumann, Gümligen (CH); Peter Nuot Frei, Dulliken (CH); Patrick Roth, Burgdorf (CH)

(73) Assignee: COMPREMIUM AG, Bern (CH)

( * ) Notice: Subject to any disclaimer, the term of this patent is extended or adjusted under 35 U.S.C. 154(b) by 7 days.

(21) Appl. No.: 18/727,262

(22) PCT Filed: Jan. 10, 2023

(86) PCT No.: PCT/EP2023/050480
§ 371 (c)(1),
(2) Date: Jul. 8, 2024

(87) PCT Pub. No.: WO2023/131724
PCT Pub. Date: Jul. 13, 2023

(65) Prior Publication Data
US 2025/0195033 A1 Jun. 19, 2025

Related U.S. Application Data

(63) Continuation-in-part of application No. PCT/EP2022/050345, filed on Jan. 10, 2022.

(30) Foreign Application Priority Data

Jan. 10, 2022 (WO) ................. PCT/EP2022/050345

(51) Int. Cl.
*A61B 8/10* (2006.01)
*A61B 3/16* (2006.01)
(Continued)

(52) U.S. Cl.
CPC .................. *A61B 8/10* (2013.01); *A61B 3/16* (2013.01); *A61B 8/0808* (2013.01); *A61B 8/488* (2013.01); *A61B 8/5223* (2013.01)

(58) Field of Classification Search
CPC ........... A61B 8/10; A61B 3/16; A61B 8/0808; A61B 8/488; A61B 8/5223; A61B 5/031
See application file for complete search history.

(56) References Cited

U.S. PATENT DOCUMENTS

2003/0152651 A1* 8/2003 Yan ...................... A61K 36/537
424/746
2013/0144185 A1* 6/2013 Fuller .................. A61B 5/7278
600/561

(Continued)

*Primary Examiner* — Bo Joseph Peng
(74) *Attorney, Agent, or Firm* — Lerner David LLP

(57) ABSTRACT

A method for determining intracranial pressure of a patient includes ultrasound imaging of a central retinal vein supplying a retina of an eye of the patient, for generating ultrasound images, exerting a varying external pressure on the eye, identifying a collapse and/or an occlusion of the central retinal vein based on the images, correlating a value of the external pressure to the collapse and/or occlusion, and determining the intracranial pressure based on the correlated external pressure value. A device includes an ultrasonic transducer, a pressure sensor and a housing with a face for contacting an eye lid and/or eye ball to exert pressure on the eye, wherein ultrasonic radiation from and to the transducer is transmitted through the face. The device includes an analyzer to process the ultrasound images and the values of the external pressure and to determine the intracranial pressure based on the correlated external pressure value.

15 Claims, 4 Drawing Sheets

(51) Int. Cl.
     *A61B 8/00*          (2006.01)
     *A61B 8/08*          (2006.01)

(56)                References Cited

U.S. PATENT DOCUMENTS

2013/0211285 A1\*   8/2013  Fuller ................... A61B 5/031
                                                       600/561
2020/0315583 A1\*  10/2020  Baumann ............. A61B 8/4281
2022/0400946 A1\*  12/2022  Mujat ................ A61B 5/14555
2024/0164653 A1\*   5/2024  Yu ........................ A61B 5/7257

\* cited by examiner

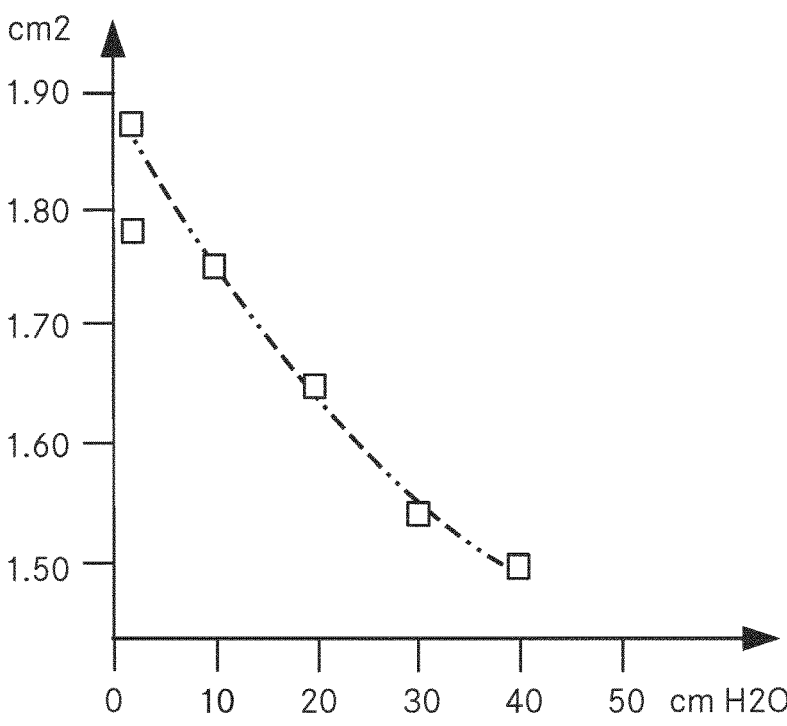
Fig. 8
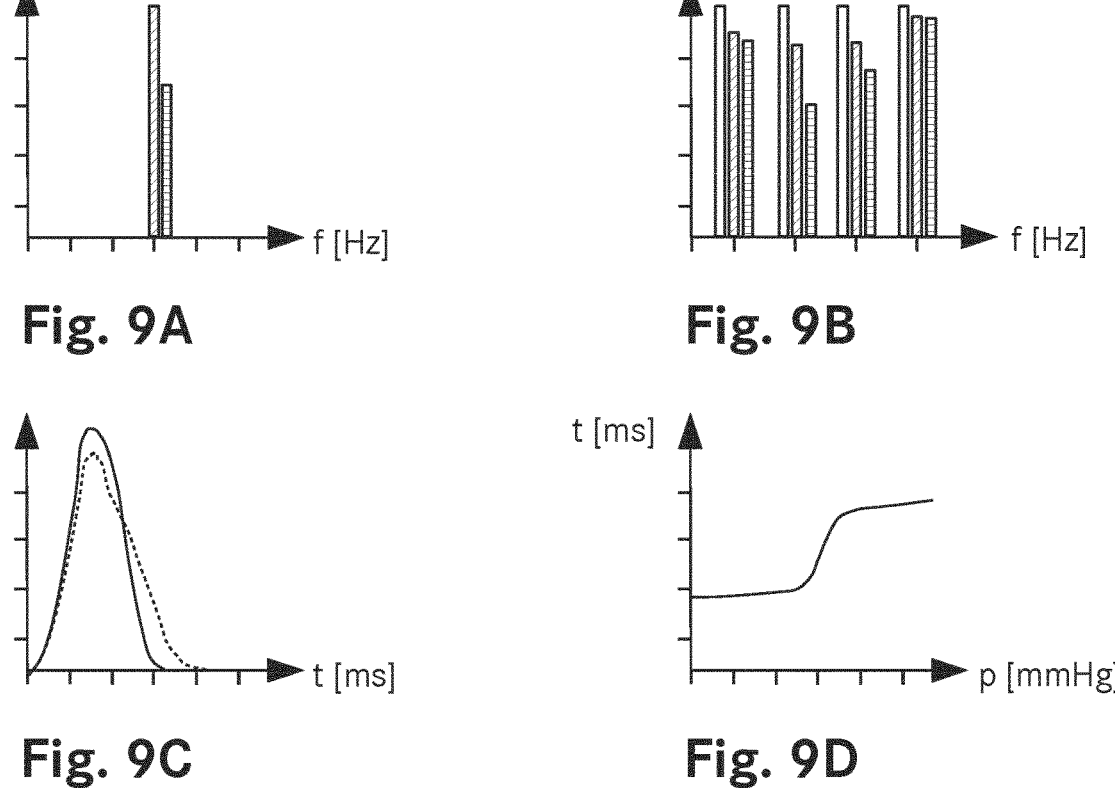
Fig. 9A
Fig. 9B
Fig. 9C
Fig. 9D

METHOD AND DEVICE FOR DETERMINING INTRACRANIAL PRESSURE OF A PATIENT

CROSS-REFERENCE TO RELATED APPLICATIONS

The present application is a national phase entry under 35 U.S.C. § 371 of International Application No. PCT/EP2023/050480, filed Jan. 10, 2023, published in English, which claims priority to Application No. PCT/EP2022/050345, filed Jan. 10, 2022, the disclosures of which are incorporated herein by reference in their entireties.

The invention relates to a method for determining intracranial pressure of a patient and to a device for determining intracranial pressure of a patient.

BACKGROUND ART

Intracranial pressure (ICP) is the pressure generated by the contents of the cranial cavity (in particular the cerebrospinal fluid) on the wall of the cranial cavity and on brain tissue. Normal ICP in supine adults is 5 to 15 mm Hg, acceptable values go up to about 20-25 mm Hg. The ICP exceeding these values (i.e. intracranial hypertension), e.g. due to a traumatic event, indicates a medical emergency as the increased pressure causes inter alia headache, ataxia, confusion, drowsiness and coma. Accordingly, treatment is required to reduce the ICP.

Intracranial pressure is directly transmitted to the intracranial venous system and the subarachnoidal space surrounding the brain. The optical nerve is part of the brain and also surrounded by subarachnoidal space. Thus, the ICP is directly transmitted to the optical nerve and the central retinal vein which furthermore drains into basic venous cisterns inside the scull.

Venous Ophthalmodynamometry is a procedure that measures the relative occlusion pressure of intraocular blood vessels by exerting a force on the globe of the eye and displaying the intraocular veins observing their collapse. This method has first been described by Baurmann 1925 (Baurmann M. Über die Entstehung und klinische Bedeutung des Netzhautvenenpulses. Dtsch Ophthalmol Ges 1925; 45:53-9) and used by Raimund Firschmann et al. measuring ICP (J Neurosurg. 2011 August; 115(2):371-4.doi: 10.3171/2011.3.JNS101275. Epub 2011 Apr. 29). Conventionally, collapse of the intraocular veins is observed by split lamp examination. However, this requires local anesthesia inducing mydriasis, which meant that important medical information, relating to the corneal reflex, is lost. Furthermore, using split lamp examination, only some branches of the central retinal vein are visible. Often, in case of an edema of the papilla, the collapse of the nerve is not reliably detectable. Due to the direct contact to the open eye, sterility has to be ensured.

Accordingly, other approaches to non-invasively measuring ICP have been proposed, inter alia in U.S. Pat. No. 9,585,578 B2 (Third Eye Diagnostics, Inc.) and WO 2004/100770 A2 (Caritas St. Elizabeth's Medical Center of Boston, Inc.), based on applying an external force on the eye and imaging the central retinal vein, e.g. by Doppler ultrasound techniques. The flow in the central retinal vein (CRV) is typically continuous with post-systolic peaks according to central artery waveform. The normal velocity in CRV may range from 2.9 to 5.7 cm/s. The occlusion of the collapsed vein, stopping the blood flow, is visible from the Doppler signal.

These approaches allow to perform the examination through the closed eye lid. However, usual Doppler ultrasound examinations are associated with a high impact on the delicate tissue of the eye and its surrounding region. This is why acoustic output exposure levels are limited for ophthalmic use to e.g. a peak intensity $I_{SPPA.3}$ of 28 W/cm2, an average intensity of $I_{SPTA.3}$ of 17 mW/cm2 or a mechanical index MI of 0.23, which limits are way below the limits for other ultrasound applications. Accordingly, usual Doppler techniques cannot just be applied to the ocular region.

Furthermore, in order to obtain the ICP the value of the external pressure applied for occluding the central retinal vein needs to be adjusted to account for the intraocular pressure (IOP). Conventionally, this requires the independent determination of the IOP, e.g. by (applanation) tonometer measurements. This complicates the examination significantly, and some of the advantages of the newer approaches, such as being able to perform the examination through the closed eye lid, are put into perspective.

SUMMARY OF THE INVENTION

It is the object of the invention to create a method and device pertaining to the technical field initially mentioned, that allow for a simple, non-invasive and precise determination of the intracranial pressure.

The solution of the invention is specified by the features of claim 1. According to the invention, the method comprises the following steps:

a) ultrasound imaging of a central retinal vein supplying a retina of an eye of the patient, for generating ultrasound images;

b) exerting a varying external pressure on the eye;

c) identifying a collapse and/or an occlusion of the central retinal vein based on the ultrasound images;

d) correlating a value of the external pressure to the collapse and/or occlusion; and e) determining the intracranial pressure based on the correlated external pressure value.

The collapse and/or occlusion of the central retinal vein may be identified from the ultrasound image data based on one or several of the following features or events, respectively:

stopping of the blood flow in the central retinal vein;

spontaneous venous pulsations in the central retinal vein;

collapse of the central retinal vein.

The pressure collapsing the intraocular veins and stopping the flow in the central retinal vein is denoted venous occlusion pressure (VOP). Due to the circumstances described above, it basically corresponds to the intracranial pressure (ICP).

Preferably, a device for determining intracranial pressure of a patient, performing ultrasound examinations and pressure measurements, includes:

a) an ultrasonic transducer;

b) a pressure sensor;

c) a housing to accommodate the ultrasonic transducer and the pressure sensor, the housing featuring a face being adapted to contact an eye lid and/or eye ball of the patient in order to exert external pressure on the eye, wherein ultrasonic radiation from and to the transducer is transmitted through the face of the housing;

d) an image processor to generate ultrasound images;

e) a display for displaying the generated ultrasound images together with a respective value of the external pressure and/or an analyzer to process the ultrasound images and the values of the external pressure in order to correlate a value of the external pressure to a collapse and/or occlusion of the central retinal vein and to determine the intracranial pressure based on the correlated external pressure value.

The ultrasonic transducer converts alternating electrical voltage into mechanical vibrations and vice versa. It may be based on piezo crystals arranged in a so-called array (ultrasonic array, piezo array).

Hand-held devices for the simultaneous acquisition of ultrasound images and pressure measurements are known, e.g. from WO 2019/106535 A1 (U. Baumann, V. Baumann) or described in copending application CH 70688/2021 of 9 Dec. 2021.

The image processor may be arranged within the housing or be part of a separate device, such as a control device that includes further processing as well as input and/or output devices, such as a touchscreen. The image processor may feature a number of individual processors (e.g. DSP, FPGA and other microcontrollers) that may be arranged within and/or outside the housing. In a preferred embodiment, the image processor comprises a first processor (e.g. a DSP, FPGA) for pre-processing the (raw) ultrasound data, which is arranged close to the ultrasound array, within the housing of the device, and a second processor for enhancing the pre-processed image data, which is arranged in a control device, separate from the housing accommodating the transducer and the pressure sensor. It may be advantageous to handle most or all of the image generation and processing within the housing, close to the ultrasonic transducer as this allows for true real-time image generation with minimal lag and/or for dynamically controlling the transducer (array) based on the most recent image data.

Compared to prior art solutions, the inventive method and device have a number of advantages. Inter alia, compared to slit lamp examinations, it is not necessary to induce mydriasis, accordingly, the corneal reflex, providing important medical information, is not impaired. Ultrasonic examinations allow for imaging flow within and occlusion of the CRV not only inside but also behind the eye. In addition, the optic nerve sheath diameter may be determined from the same image data, at different depths behind papilla. The inventive method and device are applicable in human and veterinary medicine.

Papilledema is optic disc swelling that is caused by increased intracranial pressure due to any cause. The signs of papilledema that are seen using an ophthalmoscope include a venous engorgement, which is usually the first sign (Eye Wiki, last edited on Apr. 23, 2021). This engorgement of venous outflow of eye might be not only due to elevated ICP but by congestion on the location of papilla too, leading to additional pressure on the draining veins. Thus, measuring venous outflow pressure inside the eye will probably not display real pressure in central retinal vein, which begins behind the papilla and which has direct access to intracranial vessels (basal cisterns). Therefore, it is advantageous that the ultrasound images represent a region of the central retinal vein behind a papilla region and the identification of the collapse and/or occlusion is based on an inspection of this region, preferably at locations where the optical nerve sheath diameter (ONSD) routinely is measured by ultrasound.

Preferably, the ultrasound imaging is performed through a closed eye lid of the eye of the patient. Accordingly, no local anesthesia of the eye is needed and the risk of infections is greatly reduced. Nevertheless, a sterile ultrasoundtranslucent membrane can be placed between the eye lid and the device to prevent transmission of infectious agents. The ultrasound gel should be sterile.

Preferably, the external pressure is varied in such a way that a first ultrasound image is acquired at a first external pressure value and that a second ultrasound image is acquired at a second external pressure value, where the first external pressure value is in a first range of 0-15 mbar, where the second external pressure value is in a second range of 15-60 mbar, and where a ratio between the second pressure value and the first pressure value is at least 1.5. This ensures that the measurements are taken in the relevant range and that a reliable determination of the intracranial pressure is enabled.

The corresponding force applied on the bulb of the eye is comparable to immersion of the head in water up to a maximum of 60 cm.

Preferably, the inventive method comprises the further step of determining an intraocular pressure in the eye, wherein the intracranial pressure is calculated as a sum of the external pressure and the determined intraocular pressure.

This is due to the fact that venous occlusion pressure (VOP) is the sum of two pressures, namely intraocular pressure (IOP) plus the external pressure due to the force that has to be applied to the eye collapsing intraocular veins and thus stopping the flow in the central retinal vein (CRV) behind the eye.

The CRV features an extraocular segment linked to an intraocular segment. In order to have flow between the segments, the CRV pressure is usually equal or higher than the ICP in the extraocular segment and equal or slightly higher than the IOP in the intraocular segment. Pulsations of the vein in the region of the nerve head are observable if the CRV pressure is substantially equal to the IOP. If the ICP is elevated, the CRV pressure will rise and thus pulsations of the vein—if present at normal levels of ICP—will disappear As soon as the IOP is increased by applying an external pressure, the pulsations will reappear as soon as the IOP substantially matches the ICP. This is why pulsations provide information on the actual ICP, at least in cases where the ICP is elevated.

The CRV collapses if the IOP is increased above the venous pressure, in particular by exerting an external pressure onto the eye ball. The corresponding venous occlusion pressure (VOP) is essentially equal to the pressure in the extraocular segment of the CRV and thus to the ICP. Therefore, at the collapse of the CRV, the sum of the proper IOP (without external pressure) and the applied external pressure substantially match the ICP, wherein a slight correction might be necessary because the VOP is usually slightly higher than the actual ICP.

In a first group of embodiments, the intraocular pressure is determined based on at least two measurements of the eye ball diameter in the ultrasound images, wherein the at least two measurements relate to different values of the external pressure. The eye ball will be deformed due to the external pressure, wherein a mechanical resistance of the eye ball against deformation will increase with increasing intraocular pressure, i.e. reduced deformability is directly linked to increased IOP. Feasibility studies have shown that the IOP may be quantitatively obtained from two (or more) measurements of the eye ball pressure at different external pressure.

In a second group of embodiments, the intraocular pressure is determined based on at least two measurements of a geometric property relating to a contact between a contact region of a device for the ultrasound imaging with the eye of the patient (i.e. the sclera, cornea or the eye lid), the geometric property varying with varying external pressure.

Preferably, the geometric property is at least one of the following:

a) a depth of a measuring chamber arranged behind a contact membrane of the device;

b) an area of a contact surface between the contact region and the eye.

Both properties vary with varying external pressure, wherein the variation depends from the elasticity of the eye ball and thus from the IOP. Again, feasibility studies have shown that the IOP may be quantitatively obtained from two (or more) measurements of such geometric properties at different external pressure.

Preferably, the intraocular pressure and the external pressure for collapsing and/or occluding the central retinal vein are determined in a single process. This allows for obtaining both quantities easily and reduces the load on the health professional as well as on the patient. Furthermore, it is ensured that the modalities of the determination of both the VOP and the IOP are always consistent, thus improving the reliability of deduced quantities such as the ICP.

For the essentially simultaneous determination of the IOP and the external pressure for collapsing and/or occluding the CRV essentially the same values of external pressure, such as in the ranges and with the ratios discussed above, may be employed. If the determination of the IOP is based on ultrasonic images, different image regions relating to the IOP (e.g. the eyeball) and to the VOP (e.g. the CRV and its surroundings) may be processed together or separately.

Preferably, for generating the ultrasound images underlying imaging data is processed by image enhancing. Suitable image enhancing during the generation of the image data and/or during post processing allows for substantially improving the images with regard to manual and/or automatic image analysis.

Preferably, the image is enhanced by a processor close to the ultrasound array, in particular by the image processor (DSP, particularly an FPGA) for generating the ultrasound images from the raw ultrasound data.

In preferred embodiments, the image enhancing comprises a combination of spatial and temporal processing of a temporal sequence of imaging data to magnify small movements or changes. This allows in particular for substantially improving the perceptibility of the existence or non-existence of blood flow in the CRV and/or of the spontaneous venous pulsations.

Preferably, the image enhancing comprises the steps of spatial decomposition of the imaging data, subsequent pixel-wise temporal processing of the decomposed data, including a selective amplification of spatial bands of the decomposed data, and reconstruction of the temporally processed data. A corresponding method is described in Wu et al.: "Eulerian Video Magnification for Revealing Subtle Changes in the World", ACM Transactions on Graphics, Volume 31, Issue 4, July 2012, Article No.: 65, pp 1-8.

For the selective amplification, filter criteria may be employed that match an expected frequency of the small movements to be magnified. In particular, the filter criteria may match an actual or expected heart rate of the patient. For that purpose, the filter criteria may be set to usual heart rates, i.e. 40-180/min, or the heart rate of the patient may be measured by a known device and fed to the image processor and/or analyzer in order to set the filter parameters and thus controlling the selective amplification.

Independent from the specific image enhancing process, capturing information on the pulse of the patient and/or of the operator as well as using this information for controlling the acquisition and/or processing of the image data may be helpful as artefacts due to (slight) movements of the operator's hand or the patient's tissue may be compensated and movements that are driven by the patient's pulse may be compensated or magnified depending on the desired results. Accordingly, it may be advantageous to have a device for capturing information on the pulse of the patient and/or a device for capturing information on the pulse of the operator. They may be integrated into the inventive device for the ultrasound and pressure measurements or separate from it.

Other processes for pre- and/or post-processing the raw ultrasound and/or image data may be employed such as adaptive frame rates allowing for slow motion video at least in certain time intervals or digital zooming at an early stage of the processing of the ultrasound and/or image signals in order to focus on the region of interest and reduce the computational load by disregarding pixels or image regions that are not related to this region of interest.

In first preferred embodiments, the collapse and/or occlusion of the central retinal vein is identified independent from Doppler data, in particular based on a shape of the central retinal vein in the ultrasound images. Based on the shape, a collapse of the CRV and/or an existence or non-existence of pulsation of the CRV may be identified. As mentioned above, the perceptibility of the latter may be greatly enhanced by suitable image processing. In order to enable the monitoring of pulsation, the frequency of which typically corresponding to the heart rate of the patient, it may be necessary to increase the external pressure slowly, during a period of time (compression phase) where a number of oscillations (e.g. 2-3 oscillations) are observed at every pressure bin.

Instead of the shape of the central retinal vein, the blood flow in the CRV may be observed, in particular based on suitably enhanced images.

In all cases, abstaining from using Doppler data, the energy density and thus the impact on the observed tissue may be greatly reduced.

In second preferred embodiments, the collapse and/or occlusion of the central retinal vein is identified on Doppler data relating to a blood flow in the central retinal vein. Usual Doppler ultrasound measurements are related to a considerable impact on the examined tissue—in the case of ophthalmologic examinations strict limitations are imposed, and in order to be able to perform a Doppler-assisted examination of the relevant region of tissue, additional measures such as one or several of the following may be required:

a) selective switching on and off of a generation of the Doppler data during the measuring process, i.e. Doppler data is generated only during certain time intervals, e.g. during the compression phase and/or only if it follows from the ultrasound images that the optic nerve, which is a clearly discernible structure, is in a desired imaging region; outside these time intervals standard non-Doppler images are generated, involving substantially reduced energy density;

b) restricting the generation of Doppler data to a subvolume of the captured volume for the ultrasound imaging; this is achieved e.g. by selectively using some of the elements of the transducer array; the geometry of the emitted ultrasound radiation may be chosen in such a way that particularly sensitive regions such as the retina are substantially outside of radiation with higher energy density;

c) reducing a sample volume by pulsing the ultrasound radiation.

In addition, the frequency and energy density should be carefully chosen. Assuming a depth of the region of interest of about 2.5-3 cm and a required resolution of about 0.2 mm or better, frequencies of 15 MHz or more, preferably 30 MHz or more, are preferred. Most preferably, the resolution is 0.1 mm or better at a depth of 3 cm, and/or the observable range of the blood flow velocity in the CRV comprises the interval of 0.03-3.0 cm/s. This ensures that the reduced velocities occurring prior and during to a collapse are adequately resolved, normal flow velocities in the CRV being about 1.5-4.0 cm/s. The energy density will be chosen such that the limitations for ophthalmological examinations are met. The same applies to the frame rate, where value of about 15/s appears to be suitable. Due to the favourable conditions for the transmission of ultrasound radiation, the energy density may be chosen to be rather low without impairing image quality, even at higher frequencies.

Similar to the switching on and off of the Doppler modality, parameters such as energy density or frame rate may be reduced outside of a core measuring interval.

In further preferred embodiments, the collapse and/or occlusion of the central retinal vein is identified based on measurements of sound waves in the vicinity of the central retinal vein. The veins have their own pulsating pressure wave synchronous to the heartbeat. Veins are physically communicating vessels and therefore conduct pressure waves. These can be detected in every vein in the human body. In general, the pressure exerted on the eye will be transmitted to the central retinal vein and lead to a certain compressive deformation thereof. The corresponding change in shape and/or diameter will lead to various influences on the sound propagated in the CRV. Accordingly, sound wave measurements in the vicinity of the CRV may provide additional information on the geometry or state of the CRV.

The identification of the collapse and/or occlusion may be based exclusively on the sound wave measurements or they may support other ways of identification, in particular vessel geometry and/or blood flow velocities that are directly obtained from the (Doppler) ultrasound image data, thus improving the accuracy and avoiding mistakes.

Preferably, the method further comprises the step of coupling a sound signal into the patient's head, wherein the measured sound waves comprise a contribution originating from the coupled sound signal. The properties of the signal will change due to the effects of the physiological structures propagating the sound waves. This has several advantages: The properties of the signal (including amplitudes, frequencies, pulse shapes, etc.) may be chosen in such a way, that the effects of an occlusion or collapse of the CRV are clearly derivable from the measured sound waves. These properties may be adapted in a feedback loop to obtain improved results, adapted to the specific physiological environment. It is possible to correlate the measured sound waves with the initial signal, which allows for the examination of runtimes, phase shift, spectral shift or pulse broadening. Furthermore, the filtering out of unwanted noise is facilitated.

If the exerted pressure is the only varying influence in the respective time scale (of e.g. several seconds), corresponding effects may be isolated, which allows for the detection of the collapse and/or occlusion. The process may be improved by filtering out other contributions to the measured sound waves or by processing them differently than the contributions originating from the coupled sound signal.

In particular, the sound signal is non-invasively coupled into the patient's head, using a first sound transmission element contacting an outside of the patient's head, preferably in a jugular vein region. The sound transmission element will be coupled to a sound source generating vibrations in an (audible) frequency range. By contacting the patient's head with the sound transmission element, structure-borne sound is obtained and propagated through the physiological structures of the patient's head.

Experiments have shown that the jugular vein region provides a preferable option to couple in the sound signal. It is easily identifiable and accessible from the outside, and the sound waves will be transported along the vascular axis comprising the vena jugularis interna and the arteria carotis into the skull and eventually to the CRV. In order to reliably couple in the sound signal, the first sound transmission element is applied to the side of the neck, with slight pressure on the jugular vein region.

The experiments have shown as well that frequencies in the range of 100-2'000 Hz, in particular 200-900 Hz, work well. Nevertheless, other frequencies, especially other frequencies in the audible range, are applicable as well.

The sound waves may be measured based on Doppler data from the ultrasound imaging, including power Doppler data. This simplifies the process and the inventive device. In the user interface, the results of the measurements may be included in the image data; however, preferably, they are displayed separately.

Alternatively, or in addition, the sound waves may be measured based on a sound receiver (i.e. a microphone) coupled to a second sound transmission element contacting an eye region of the patient. The eye region comprises in particular the eye lid and/or eye ball of the patient.

In this case, a sound receiver for the measurements of sound waves in the vicinity of the central retinal vein is preferably arranged in or on the housing of the device according to the invention. In particular, it is coupled to the face of the housing being adapted to contact the eye lid and/or eye ball of the patient. The sound receiver may be a separate microphone, or an existing pressure sensor for measuring the pressure exerted onto the eye serves in parallel as the sound receiver.

The measurement results obtained using the sound receiver may be displayed on a user interface of the inventive device. Alternatively or in addition, they may be played back through a loudspeaker or headphones. In order to improve the aural processing of the measurements, they may be frequency-shifted, in particular to a frequency in the range of about 200-1,000 Hz, if their main frequencies are above or below that range.

The collapse and/or occlusion may be identified in particular based on one or several of the following properties:
   a) a change of an intensity (amplitude) of the measured sound waves;
   b) a change of a runtime of the sound from an origin, i.e. the runtime of the sound signal is measured, e.g. based on autocorrelation, and changes in the runtime are determined;
   c) a phase shift compared to an original signal, i.e. again the measured signal is compared to the original signal;
   d) a spectral shift compared to the original signal;
   e) an impact to a pulse shape of a pulsed sound signal.
   With respect to option d), multi-frequency signals may be used, and the spectral composition of the original signal may be compared to that of the measured signal, e.g. by comparing spectra obtained by FFT. However, in principle, a single frequency original signal may be employed, and harmonics created by the transmission through the physiological tissue may be examined to obtain information on the collapse and/or occlusion. In both cases, deformation of the CRV will change its acoustic filter characteristics, leading to different impacts on different parts of the spectrum and to a different harmonic spectrum.

As to option e), if the initial sound signal comprises distinct pulses, information on a collapse or occlusion may be obtained from a comparison between the profiles of the initial sound signal and the measured signal.

In order to compare the original signal with the measured signal, different mathematical methods, including convolution or folding, may be employed.

Disturbing sound sources from the environment may negatively affect the measurement of the transmitted sound wave. This can be prevented by the measurement of sound waves in the vicinity of the CRV of the other eye. If the measured sound wave in the other eye is subtracted from the measured sound wave from the eye to which the pressure is applied by the operator, the result is a sound wave signal without or at least with greatly reduced disturbing ambient noise.

In addition, unwanted contributions to the measured signals may be filtered out by suitable filters. For instance, a low-frequency component arising from the varying external pressure onto the eye (typically a few Hz) may be filtered out by subjecting the measured signal to a high-pass filter. As a matter of course, if a single-frequency signal is coupled in and if the harmonics are not needed, a band pass filter passing frequencies around the frequency of the initial single-frequency signal may be used.

In further preferred embodiments, non-consecutive ultrasound data associated to a same bin of external pressure are combined to generate improved ultrasound images, i.e. image data from non-neighboring frames that nevertheless relate to the same bin of external pressure is combined. This allows for improving the statistics and thus reducing noise. If the identification of collapse or occlusion is based on movements such as blood flow or CRV pulsations, it is necessary to avoid impairment of the movement information due to the combination.

Preferably, a flexible membrane is arranged on the face of the housing and the ultrasonic transducer and the flexible membrane are arranged on the housing in such a way that ultrasound radiation is transmittable from and to the ultrasonic transducer through the flexible membrane.

Preferably, a fluid-filled chamber is arranged behind the flexible membrane, the ultrasonic transducer and the pressure sensor being arranged at least partially in the fluid-filled chamber.

Both the use of the membrane as well as of the fluid-filled chamber (in particular liquid-filled chamber) provides a compliant contact surface, minimizing local deformation of the bulbus during examination.

Preferably, the chamber is formed between the membrane and a rear partition wall. The partition wall may constitute a support plate, wherein the ultrasonic transducer and the pressure sensor are arranged on the support plate such that a first transmission surface of the ultrasonic transducer and a second transmission surface of the pressure sensor are directed toward the chamber.

The pressure sensor is thus suitable for measuring a substantially static pressure prevailing in the chamber, which results in particular from the pressing force of the device against an examined object, e.g. the eye lid and thus the eye ball.

Preferably, the front main surface of the partition wall facing the chamber is flat, but this is not mandatory; in principle, it can also have convex and/or concave sections.

The ultrasonic transducer and the pressure sensor can be arranged on the partition wall in such a way that their transmission surfaces (which are formed, for example, by the respective end face or form part thereof) are flush with a front main surface of the wall. However, the front or measuring surface may also be protruding with respect to the front main surface. The measuring surface of the pressure sensor can be arranged behind the front main surface, i.e. set back. In the case of the ultrasonic transducer, it must be ensured in such an arrangement that the radiation and reception of the ultrasonic vibrations is not impeded. Preferably, the first transmission surface of the ultrasonic transducer is positioned in front of the front main surface.

In particular, the housing forms a handle so that the device can be used in a hand-held manner similar to a common ultrasound probe, whereby the application of pressure to the surface of the examined object is also performed manually. In other embodiments, the device comprises a mechanism to selectively automatically generate desired values of external pressure. In these cases it may be advantageous if the device can be mounted to the head of the patient in order to avoid relative displacement of the ultrasound array and the examined region of interest. The mechanism to generate the external pressure may increase the pressure in the fluid-filled chamber and/or feature mechanical, pneumatic or hydraulic means (e.g. bladders) to build up the desired pressure.

The membrane is ultrasonically permeable and is preferably made of such a flexible material that forces acting from the outside are transmitted directly to the chamber behind it, i.e. that no appreciable energy has to be expended for deformation of the membrane at the usual impact forces in the course of examinations carried out with the device. In the case of a comparatively soft membrane with a hardness of 50 Shore A or less, in particular 45 Shore A or less, it is ensured that a sufficiently large area of the membrane is in contact with the eye lid or sclera or cornea, respectively, even at low contact forces, so that the ultrasonic waves can be reliably transmitted between the device and the eye of the patient. Silicone rubber is particularly suitable as a material for the membrane. The thickness of the membrane in its active, front area, which serves to contact the object to be examined, is ideally 0.3-0.7 mm, in particular 0.4-0.6 mm.

The membrane may form the contact surface with the object under examination, or it may be covered by another flexible and ultrasound-permeable element during the examination, e.g., a replaceable sterile cap for single-use or single-patient-use, which ensures hygienic conditions during the examination of patients.

In addition to the membrane and the support plate, other components can be involved in sealing the chamber, on the one hand specific seals, and on the other hand, for example, elements of the housing.

The integration of both sensors in a common chamber enables a compact design of the device according to the invention and a simple and thus easily cleanable outer shape.

Preferably, the membrane has a circular base surface. The base surface extends perpendicular to a longitudinal axis of the device. This results in an isotropic deformation of the membrane, independent of an angle of the impact force with respect to the longitudinal axis, which is particularly important when the device is placed at an angle to the longitudinal axis on the site to be examined.

In the filled state, the active front area of the membrane has in each diametrical cross-section in particular a course corresponding to that of a chain function. This geometry results when the membrane is prestressed due to the filling of the contact liquid, if the membrane has a circular base, it is made of the same material over its entire surface in the active area, and the membrane thickness is constant in this area, provided that the attachment of the membrane to further elements of the device is done in such a way that no non-radial prestresses are generated in its active area. Preferably, the membrane is preformed, i.e. its shape changes only slightly as a result of filling.

Preferably, the ultrasonic transducer is attached centrally to the transition wall, and the pressure sensor is attached off-center to the transition wall. The ultrasonic transducer is thus arranged in the area of the center to enable the best possible radiation and recording of ultrasonic waves. In the case of a circular partition wall, a center of the transducer in particular substantially coincides with the center of the circle. Due to the isotropic distribution of the static pressure in the liquid contained in the chamber, the exact positioning of the pressure sensor has no influence on its measurement precision.

For use of the device according to the invention, the chamber is filled with an ultrasonically transparent liquid. Advantageously, the ultrasonically transparent liquid is an oil with a viscosity in a viscosity class of 32-68 ISO VG. In particular, the oil can be a synthetic, mineral and/or vegetable oil. The viscosity is determined according to DIN ISO 3448:2010.

In particular with hand-held devices it is preferable if movements of the device for the ultrasound imaging are compensated based on a positional sensor associated with the device. Accordingly, a sensor unit for determining a position of the ultrasonic transducer is preferably arranged in or on the housing of the inventive device, and the image processor is controlled to compensate movements of the ultrasonic transducer for the ultrasound imaging, based on the determined position. Accordingly, impacts on the image due to inadvertent movements of the device 1 by the operator (including movements caused by the operator's pulse, by tremor, etc.) are filtered out.

In particular, the positional sensor determines the inclination of the device about at least two Euler angles, perpendicular to the longitudinal axis of the device. Advantageously, the compensation of the movements is such that the generated ultrasonic images always represent the same predetermined region of tissue, i.e. that the images are aligned with respect to each other. Preferably, the compensation is part of the generation of the ultrasound images (i.e. preprocessing) such that the all further steps including visual inspection and/or post-processing are based on the aligned images.

Other advantageous embodiments and combinations of features come out from the detailed description below and the entirety of the claims.

BRIEF DESCRIPTION OF THE DRAWINGS

The drawings used to explain the embodiments show:

FIG. 8 a diagram showing the relationship between an area of the contact surface between the device and the eye and the intraocular pressure; and FIG. 9A-D diagrams showing relevant properties for the identification of a collapse and/or an occlusion based on acoustic measurements.

In the figures, the same components are given the same reference symbols.

PREFERRED EMBODIMENTS

Figure 1:
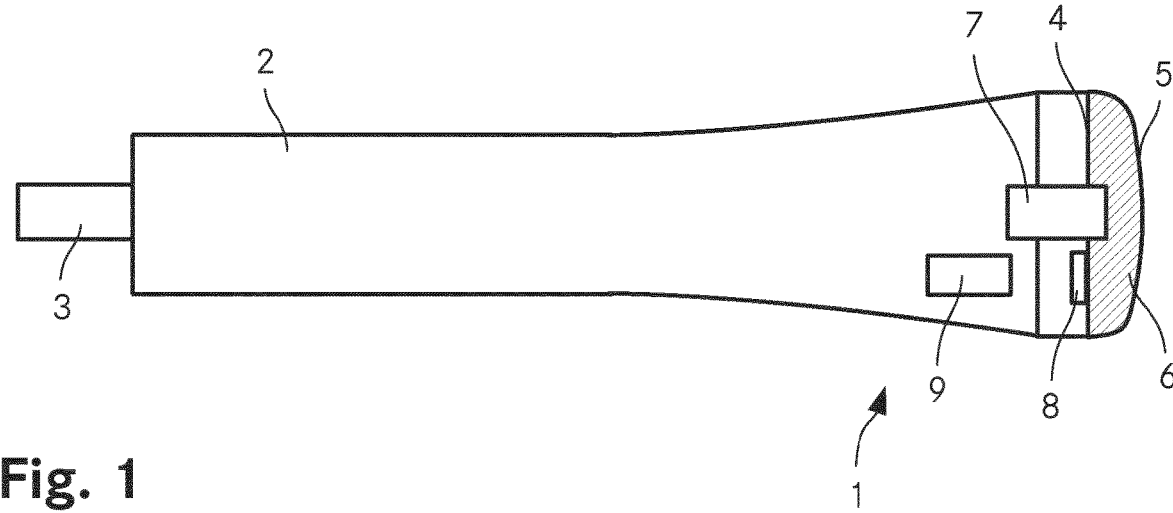
FIG. 1 a schematic cross-section of an embodiment of the inventive device.

The FIG. 1 is a schematic cross-section of an embodiment of the inventive device. The device 1 features a housing 2 accommodating electronics for controlling the electronic components of the device 1 as well as for (pre-)processing the acquired image and pressure data. A cable connector 3 is arranged at a rear end of the housing for attaching a cable to supply the device with electricity as well as to transmit control and measurement data between the device 1 and a control device, wherein the control device features inter alia a touchscreen for displaying the acquired ultrasound images as well as measurement data and for receiving control inputs of an operator.

In a front region, the housing 2 of the device 1 features a partition wall 4. Together with a membrane 5, the partition wall 4 delimits a chamber 6 accommodating a liquid. An ultrasound array 7 as well as a pressure sensor 8 are mounted on the partition wall 4. The ultrasound array 7 transmits and receives ultrasound radiation through the chamber 6 and the membrane 5, whereas the pressure sensor 8 measures a pressure in the chamber 6.

The membrane 5 is made from silicon rubber having a hardness of 40 Shore A. Its thickness is 0.5 mm. It has a circular shape with a diameter of 35 mm. The membrane 5 is preformed even in an empty state of the chamber 6 with a cross-sectional shape corresponding to a circular arc having a radius of curvature of 70 mm. As soon as the chamber 6 is filled, the cross-section of the membrane will assume the form of a catenary. The liquid contained in chamber 6 is a synthetic lubricating oil of viscosity class 46 ISO VG approved for use in the pharmaceutical sector.

The device 1 further comprises a positional sensor 9 determining the inclination of the housing 2 and thus of the ultrasound array 7 in two planes that are normal to each other and include the longitudinal axis of the housing 2, i.e. two respective Euler angles are determined and fed to the electronics for generating the ultrasound images.

Accordingly, the operator holding the housing 2 of the device 1 may manually exert mechanical pressure on a surface to be examined, wherein the pressure is transmitted through the membrane 5. The resulting additional pressure is measured by the pressure sensor 8. At the same time, the ultrasound array 7 transmits ultrasound radiation to and behind the surface to be examined, through the chamber 6 and the membrane 5 and echoes are received by the ultrasound array 7. Based on the signals, an ultrasound image is generated and displayed on the touchscreen of the control device.

Figure 2:
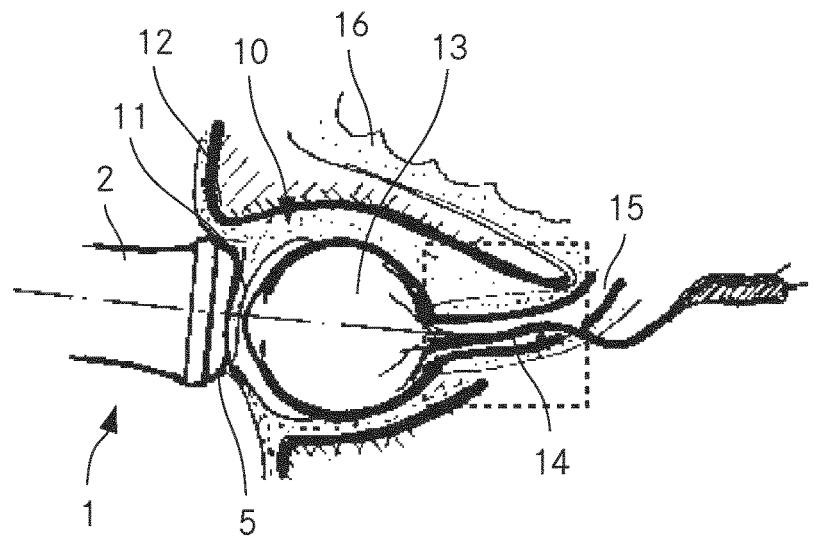
FIG. 2 an illustration showing the application of the device.

The FIG. 2 is an illustration showing the application of the device in an examination procedure. Prior to performing the examination, the eye lid 11 of the eye 10 of the patient is closed. The device 1 is supported and guided in an edge region of the front surface thereof by the upper osseous rim 12 of the frontal bone, the shapes and dimensions of the device's front and the membrane are chosen such that such guidance is facilitated.

The membrane 5 contacts the outer surface of the eye lid 11. Now, the operator may examine the eye 10 and in particular the regions behind the eye ball 13 by acquiring ultrasound images. Of particular importance for the present invention are the central retinal vein 14, the optical nerve 15, and the liquor space 16. The region of interest from where image information is needed is marked by the dashed rectangle.

At the same time, external contact pressure may be exerted by applying a respective pushing force to the housing 2 of the device 1.

The operator starts with exerting a certain minimal pressure, sufficient to ensure adequate transmission of the ultrasound radiation between the device 1 and the eye 10 of the patient. The membrane 5 of the inventive device 1 is smooth and flexible, and the fluid-filled chamber 6 allows unhindered deformation of the contact surface. Accordingly, the pressure applied on the eye is transmitted without local deformation of the bulbus. The pressure is increased, and at the same time the central retinal vein 14 is observed to identify a collapse or occlusion of the vein in the generated ultrasound images. As soon as such an event is noticed, the operator issues a confirmation by pressing a respective button on the touchscreen user interface. The corresponding value of the external pressure is stored and used for the determination of the intracranial pressure. Simultaneous with the determination of this value the intraocular pressure is measured using one of the methods discussed below.

In order to improve image quality, the inclination of the device 1 is continuously determined by the positional sensor 9. Corresponding units are publicly described and commercially available (cf. e.g. K. L. Khaw et al.: "Probe Position Sensor to Track Image Location in 2D Ultrasound", Ultrasonics, April 2020: 103). The positional sensor 9 determines the inclination about at least two Euler angles perpendicular to the longitudinal axis of the device 1, and the image data is correspondingly corrected in real-time by an FPGA arranged within the housing 2 of the device 1. At the same time and by the same FPGA, the image data is pre-processed by an optical zoom process, ensuring that exactly the region of interest and thus always the same predetermined region of tissue is further processed. Accordingly, impacts on the image due to inadvertent movements of the device 1 by the operator (including movements caused by the operator's pulse, by tremor, etc.) as well as due to the axial movement of the device 1 when increasing the external pressure are filtered out.

The pre-processed image data is further processed by a processor arranged in the control device to improve the perceptibility of the relevant aspects, wherein the same or different processes may be employed for enhancing the image date in view of visual inspection and/or automatic analysis. In particular, small changes of the shape of the CRV or in the vicinity thereof are magnified by the method described in Wu et al.: "Eulerian Video Magnification for Revealing Subtle Changes in the World", ACM Transactions on Graphics, Volume 31, Issue 4, July 2012, Article No.: 65, pp 1-8. This method involves a combination of spatial and temporal processing of the video data to specifically magnify small movements or changes. First, the data is submitted to spatial decomposition, subsequently the decomposed data is processed temporally pixel by pixel, whereas this step includes a selective amplification of spatial bands of the decomposed data, based on a frequency filter tuned to the usual heart rates of patients (as described above, fine tuning of the filter may be supported by measuring the heart rate of the patient and/or of the operator). Finally, the temporally processed data is reconstructed to obtain the enhanced image.

Further methods may be used to enhance the image data, based on standard image processing algorithms and/or machine learning based techniques, e.g. supported by deep Convolutional neural networks.

Instead or in addition to the movement compensation described above and/or the image enhancement by motion magnification, further methods such as those described in M. Yazdi et al.: "New Trends on Moving Object Detection in Video Images Captured by a moving Camera: A Survey", Computer Science Review, Elsevier, 2018, 28, pp. 157-177.

In the context of the described embodiment, the intracranial pressure (ICP) is obtained as a sum of the intraocular pressure (IOP) with the external pressure required to collapse the CRV. Therefore, the IOP is determined simultaneously with the acquisition of the ultrasonic images at different values of external pressure.

Two exemplary methods of determining the intraocular pressure (IOP) using the inventive device are described in the following. The feasibility thereof has been studied on cadaver eyes as well as on test persons. In contrast to prior art methods, such as applanation tonometry, where pressure is applied to the eye and the flattening of the corneal curvature is measured, no direct contact with the open eye and therefore no anesthesia of the eye is required. Furthermore, the IOP as well as the external pressure required for occlusion of the central retinal vein (CRV) may be determined in a single process, substantially at the same time.

In the first of the two methods, structures within the eye are measured using ultrasound, through the closed eyelid. The inventive device allows for visualizing and measuring pressure-related changes in the examined tissue in real time and quantitatively correlating those changes to the value of the applied pressure. The eye as a fluid-filled space shows ideal conditions for such measurements. This is also true with the eye closed as ultrasound is able to provide excellent images through the eyelid. This eliminates the need for direct contact with the open eye and the necessary local anesthesia.

Figure 3:
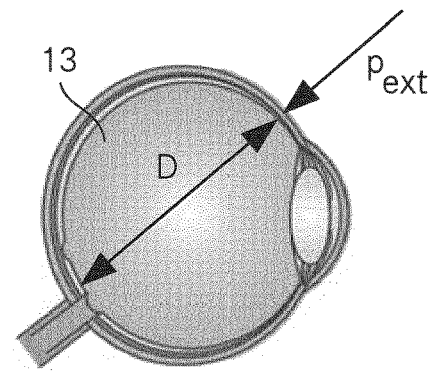
FIG. 3 an illustration of the measurement of the diameter of the eye ball.

Now, using the inventive device, the absolute eye diameter D and/or its relative change is directly measured based on the generated ultrasound images, at several values of external pressure $p_{ext}$ exerted on the eye ball 13 (cf. FIG. 3).

In the feasibility study, frozen cadaver eyes of cattle were thawed and connected to a riser tube system with NaCl 0.9% using a venflon. By varying the water column, the pressure in the eye was adjusted. External pressure was applied to the eye with the inventive device, and the diameter of the eyeball was determined based on the generated ultrasound images.

Figure 4:
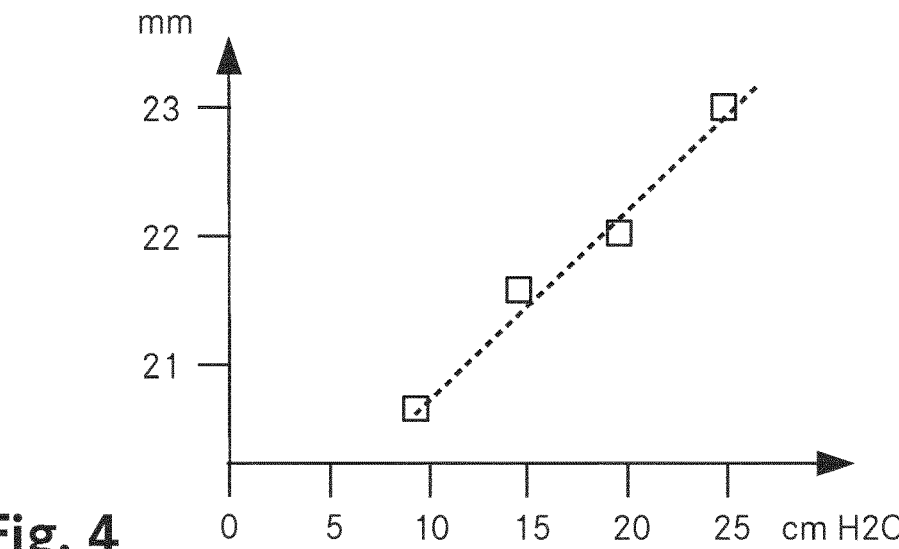
FIG. 4 a diagram showing the relationship between the intraocular pressure and the diameter of the eye ball.
Figure 5:
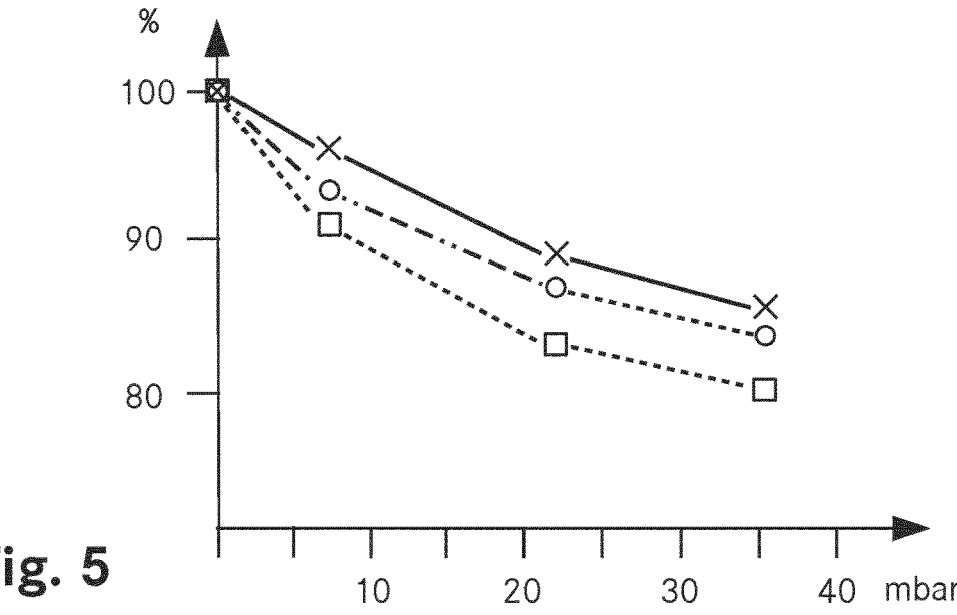
FIG. 5 a diagram showing the relationship between the diameter of the eye ball and an external pressure exerted on the eye, at different intraocular pressures.

The FIG. 4 shows the relation between the intraocular pressure (on the horizontal axis, in cm $H_2O$) and the diameter (on the vertical axis, in mm). With increasing intraocular pressure the diameter of the eye increases, wherein the increase is substantially linear. Now, the FIG. 5 displays the decrease of the diameter with different intraocular pressures and an increasing pressure on the eye by the inventive device. The horizontal axis denotes the external pressure in mbar, whereas the vertical axis denotes the reduction of the diameter in %. The solid curve and the crosses relate to an intraocular pressure of 30 cm $H_2O$, the dot-dashed curve and the circles relate to an intraocular pressure of 20 cm $H_2O$, whereas the dashed curve and the squares relate to an intraocular pressure of 5 cm $H_2O$. As can be seen from the Figure, the decrease of the eye diameter depends on the intraocular pressure and the external pressure applied to the eye.

Figure 6:
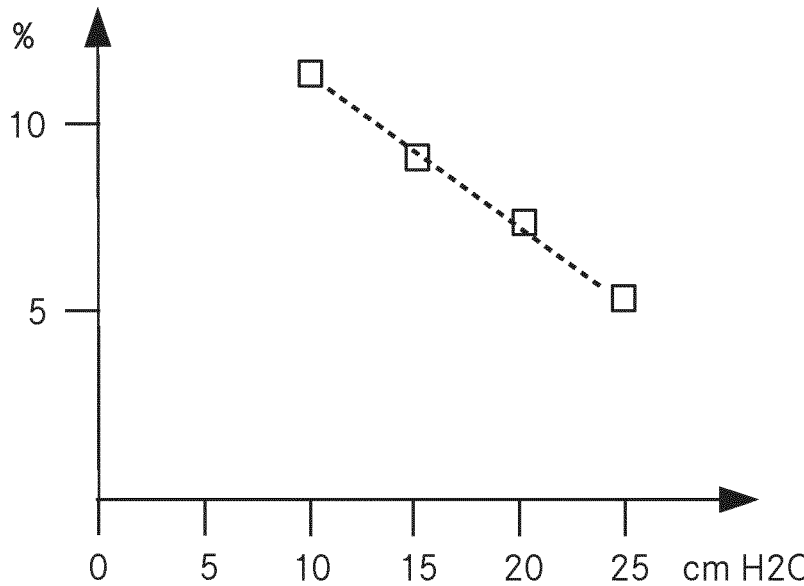
FIG. 6 a diagram showing the relationship between the decrease of the diameter of the eye ball and the intraocular pressure.

The FIG. 6 shows the relation between the decrease of the eye diameter (vertical axis, in %) and the intraocular pressure (horizontal axis, in cm $H_2O$), when applying an external force of 30 mbar to the eye. As can be seen from the Figure, the relation is clearly linear, at least in the examined pressure range. Thus, the intraocular pressure can be measured by the described method. In the shown example, at an external pressure of 30 mbar, the relation between the increase of intraocular pressure and the decrease of the compression in % is 0.42.

In a second method, ultrasound measurements are not needed for the determination of the intraocular pressure, but the depth of the chamber situated behind the membrane of the inventive device and/or the contact surface of the membrane on the eye (lid) is measured at different values of external pressure. As shown in FIG. 2, during the measurement process the membrane of the inventive device contacts the eye lid 11 and the operator exerts an external pressure on the eye lid, applying a forward directed force onto the inventive device 1.

Figure 7:
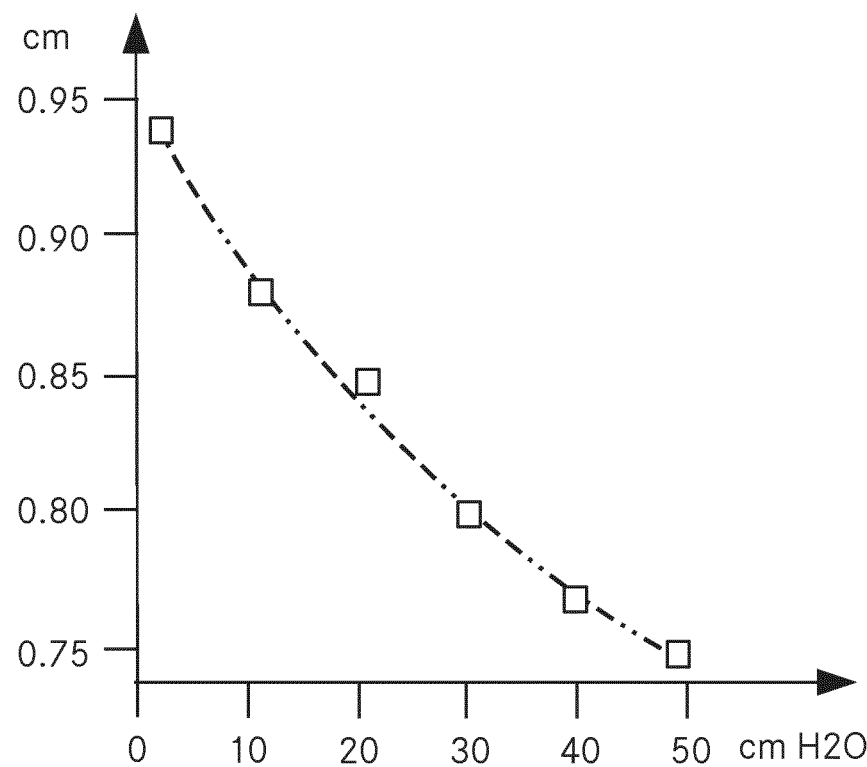
FIG. 7 a diagram showing the relationship between the depth of a measuring chamber of the device and the intraocular pressure.

The FIG. 7 shows the relation between the depth of the measuring chamber (vertical axis, in cm) and the intraocular pressure (horizontal axis in cm $H_2O$) at an external contact pressure of 30 mbar. With increasing intraocular pressure, the depth of the measuring chamber decreases almost linearly.

The same applies to the contact area between the membrane and the eye (lid), as can be seen from FIG. 8 showing the relationship between the contact area (vertical axis, in $cm^2$) and the intraocular pressure (horizontal axis in cm $H_2O$) at an external contact pressure of 30 mbar.

Accordingly, it is possible to determine the intraocular pressure based independently from the ultrasound image, based solely on effects on the inventive device itself.

The depth of the chamber and the contact area may be measured with known methods such as laser interferometry, capacitive sensors or based on optical images.

FIGS. 9A-D are diagrams showing relevant properties for the identification of a collapse and/or an occlusion based on acoustic measurements. Basically, a sound signal is coupled into the patient's head in a jugular vein region of the neck. A sound transmission element coupled to a piezoelectric sound generator is slightly pressed against the patient's skin, such that the sound signal is transmitted through the patient's tissue as a structure-borne sound. It eventually reaches the central retinal vein (CRV). In the context of performed experiments, inter alia sinusoidal oscillations at a frequency of 440 Hz have been used. It has been shown that these are reliably transmitted through the vascular axis including the vena jugularis interna and the arteria carotis to reach the CRV.

In a vicinity of the CRV, in particular from the eyeball, the sound waves are picked up as a measurement signal. As described above, in the course of an examination, the operator increases the pressure onto the eye and observes the central retinal vein in the ultrasound images to detect the collapse or occlusion of the vein. Tests have now shown that this process may be improved by taking into account the measured acoustic signal.

In FIG. 9A, amplitudes of measured acoustic signals obtained at different external pressures are compared. A collapse or occlusion of the CRV is assumed to lead to a prominent drop in amplitude. Therefore, if such a drop is observed, it may be derived that the collapse or occlusion is happening.

In FIG. 9B, the spectra of a multi-frequency signal at the origin (i.e. the site where it is coupled into the patient's head) (white box), in in the vicinity of the CRV, at a first, lower external pressure (oblique hatched) and at a second, higher external pressure, where the CRV is collapsed (horizontally hatched) are shown. Depending on the frequency, the signal components experience different levels of attenuation, when travelling through the patient's tissue. Comparing the spectra relating to the low and high external pressure, one notices that there is a prominent drop in amplitude at a frequency value represented by the second set of boxes. Therefore, a prominent decrease at the corresponding frequency, compared to the less prominent decreases at other frequencies might be an indication for the CRV collapse.

In FIG. 9C, the profile of an acoustic signal consisting of a sequence of pulses is examined. The solid line represents a pulse as measured at a low external pressure, where the flow in the CRV is not materially affected. The dashed line represents a pulse as measure at a higher external pressure, which caused the CRV to collapse. As can be seen, with increasing pressure the amplitude of the signal decreases. In addition, the width of the pulse increases and there is a characteristic change in the pulse profile. Again, these characteristics might be correlated with collapse of the CRV.

FIG. 9D illustrates the runtime (vertical axis) of a signal as a function of the external pressure. In a first (small) pressure range, the influence of the external pressure on the runtime is marginal. The same applies to a third (high) pressure range. However, in a transition range between the first and third range, the runtime significantly increases. This transition range (or a specified point in time related to this range) may be identified to obtain the venous occlusion pressure (VOP).

The invention is not limited to the described device and methods. In particular, instead of a hand-held device the invention may be executed with a device that is attached to the patient's head, e.g. by temples, similar to an eyeglass, by a headband or similar. Similarly, a hand-held device may feature a support, e.g. a ring surrounding the eye to be examined or a plate resting on the patient's forehead.

Electronic components for image pre-processing (i.e. in the context of image generation) and for post-processing (i.e. based on existing image data) may be arranged within the housing of the hand-held probe, close to the ultrasound array, and/or within the control device.

The external pressure may be exerted manually by the operator or it may be automatically generated, e.g. by an inflatable bladder or other pneumatic or hydraulic means. As an alternative, mechanical means may be employed.

In summary, it is to be noted that the invention creates a method and device that allow for a simple, non-invasive and precise determination of the intracranial pressure.

The invention claimed is:

1. A method for determining intracranial pressure of a patient, comprising the following steps:
    a) ultrasound imaging of a central retinal vein supplying a retina of an eye of the patient, for generating ultrasound images;

b) exerting a varying external pressure on the eye;

c) identifying a collapse and/or an occlusion of the central retinal vein based on the ultrasound images;

d) correlating a value of the external pressure to the collapse and/or occlusion; and e) determining the intracranial pressure based on the correlated external pressure value;

wherein the collapse and/or occlusion of the central retinal vein is identified on Doppler data relating to a blood flow in the central retinal vein, wherein an impact of ultrasound radiation related to the ultrasound imaging is reduced by at least one of the following measures:

a) selective switching on and off of a generation of the Doppler data during the measuring process;

b) restricting the generation of Doppler data to a subvolume of the captured volume for the ultrasound imaging; or c) reducing a sample volume by pulsing the ultrasound radiation.

2. The method as recited in claim 1, wherein the ultrasound images represent a region of the central retinal vein behind a papilla region and wherein the identification of the collapse and/or occlusion is based on an inspection of this region.

3. The method as recited in claim 1, wherein the ultrasound imaging is performed through a closed eye lid of the eye of the patient.

4. The method as recited in claim 1, wherein the external pressure is varied in such a way that a first ultrasound image is acquired at a first external pressure value and that a second ultrasound image is acquired at a second external pressure value, where the first external pressure value is in a first range of 0-15 mbar, where the second external pressure value is in a second range of 15-60 mbar, and where a ratio between the second pressure value and the first pressure value is at least 1.5.

5. The method as recited in claim 1, further comprising a step of determining an intraocular pressure in the eye, wherein the intracranial pressure is calculated as a sum of the external pressure and the determined intraocular pressure.

6. The method as recited in claim 5, wherein the intraocular pressure is determined based on at least two measurements of the eye ball diameter in the ultrasound images, wherein the at least two measurements relate to different values of the external pressure.

7. The method as recited in claim 5, wherein the intraocular pressure is determined based on at least two measurements of a geometric property relating to a contact between a contact region of a device for the ultrasound imaging with the eye of the patient, the geometric property varying with varying external pressure.

8. The method as recited in claim 7, wherein the geometric property is at least one of the following:

a) a depth of a measuring chamber arranged behind a contact membrane of the device; or b) an area of a contact surface between the contact region and the eye.

9. The method as recited in claim 5, wherein the intraocular pressure and the external pressure for collapsing and/or occluding the central retinal vein are determined in a single process.

10. The method as recited in claim 1, wherein for generating the ultrasound images underlying imaging data is processed by image enhancing.

11. The method as recited in claim 10, wherein the image enhancing comprises a combination of spatial and temporal processing of a temporal sequence of imaging data to magnify small movements or changes.

12. The method as recited in claim 11, wherein the image enhancing comprises the steps of spatial decomposition of the imaging data, subsequent pixel-wise temporal processing of the decomposed data, including a selective amplification of spatial bands of the decomposed data, and reconstruction of the temporally processed data.

13. The method as recited in claim 1, wherein the collapse and/or occlusion of the central retinal vein is identified independent from Doppler data, in particular based on a shape of the central retinal vein in the ultrasound images.

14. The method as recited in claim 1, wherein non-consecutive ultrasound data associated to a same bin of external pressure are combined to generate improved ultrasound images.

15. The method as recited in claim 1, wherein movements of a device for the ultrasound imaging are compensated based on a positional sensor associated with the device.

* * * * *